United States Patent [19]

Yin et al.

[11] 4,139,415

[45] Feb. 13, 1979

[54] IN VITRO METHOD OF DETERMINING THE BIOLOGICAL ACTIVITY OF FACTOR Xa INHIBITOR IN BLOOD

[75] Inventors: Ee T. Yin, St. Louis, Mo.; Oddvar Tangen, Uppsala, Sweden

[73] Assignee: Pharmacia AB, Uppsala, Sweden

[21] Appl. No.: 744,227

[22] Filed: Nov. 23, 1976

[30] Foreign Application Priority Data

Dec. 1, 1975 [SE] Sweden ................................ 7513495

[51] Int. Cl.$^2$ ...................... G01N 31/14; G01N 33/16
[52] U.S. Cl. ............................................ 195/103.5 R
[58] Field of Search ................................ 195/103.5 R

[56] References Cited

U.S. PATENT DOCUMENTS

| | | | |
|---|---|---|---|
| 3,884,896 | 5/1975 | Blomback et al. | 195/103.5 R |
| 3,985,618 | 10/1976 | Innerfield | 195/103.5 R |

*Primary Examiner*—Alvin E. Tanenholtz
*Attorney, Agent, or Firm*—Fred Philpitt

[57] ABSTRACT

The present invention concerns an in vitro method for the determination of the plasma inhibitor to activated Factor X (XaI), which is an alpha-2-globulin of molecular weight 58,000-65,000, and which has been termed variously as antithrombin III, heparin cofactor and alpha-2-antitrypsin.

7 Claims, No Drawings

IN VITRO METHOD OF DETERMINING THE BIOLOGICAL ACTIVITY OF FACTOR XA INHIBITOR IN BLOOD

BACKGROUND

There exists at present no satisfactory biochemical technique for the early recognition of incipient of overt thrombotic state in man or animal. Thromboembolic disease is becoming an increasingly important cause of disability and death as advances in surgical procedures open way to more extensive surgery, and the wide use of estrogen containing compounds as oral contraceptives.

In recent years much experimental data both in vitro and in vivo have appeared in the literature suggesting that the efficacy of XaI as a naturally occurring anticoagulant during blood coagulation is dependent more upon its inactivation of initially generated Factor Xa thereby preventing thrombin formation, rather than preventing thrombin from attacking fibrinogen. This view is especially strengthened by the report that trace amounts of heparin could markedly enhance the inhibition of Factor Xa by XaI.

Certain circumstantial evidence strongly suggests that during and post surgery, a state of the so-called "hypercoagulability" previously absent, is created in some patients. But this hypercoagulable state will remain non thrombonic as long as the rate of Factor Xa removal by XaI exceeds that of Factor Xa formation. It has also been claimed that women on oral antiovulatory agents are more prone to thrombose as a result of injury because of lowering in their blood of XaI.

This information has raised the possibility that low levels of XaI may reflect hypercoagulability. Therefore it may be suggested that plasma XaI activity might be a practical marker of hypercoagulable state. This hypothesis is further strengthened by the following observations:

(a) patients congenitally deficient in antithrombin III (XaI) are thrombophilic, (b) Women on oral contraceptive agents who have low XaI activity in their plasma, as a group, have a higher incidence of post operative deep vein thrombosis, than those who are not on the "pill".

Therefore there is a great need for a specific method of determining the biological activity of XaI in blood plasma.

There are some methods available which try to determine the XaI activity. The most frequently used methods are based upon immunological determination and the inhibition of thrombin. However these techniques have several disadvantages. Thus, the immunological method, although it will detect the antigen $\alpha_2$-globulin does not indicate this inhibitor's biological activity. It has been reported that certain patient's blood, congenitally deficient in this inhibitor's biological activity, showed no defiency as measured by the immuno assay. (Sas et al., Thromb. Diath. Haemorrh. 32 (1974) p. 105).

The thrombin method for this inhibitor is not specific because at the same time it measures the activity of other serum proteinase inhibitors. (Whigham et al. Thromb. Diath. Haemorrh. 34 (1975) p. 365). Moreover it is sensitive to very small amounts of heparin and heparin-like substances and fibrinogen degradation products present in the blood plasma.

THE PRESENT INVENTION

Now we have quite surprisingly found that the biological activity of XaI in blood may be determined in vitro without these disadvantages when using the method according to the present invention, in which method a blood plasma sample is incubated with a polysaccharide polysulphate and with activated factor X (Xa), for a pre-determined period and thereafter the residual amount of Xa activity is determined in a per se known manner.

The residual amount of factor Xa may be determined by using fibrin formation as the end point (measuring the clotting time) according to the method well-known in the art. It may also be determined by measuring the esterase or amidolytic activity by using other suitable substrates.

The polysaccharide polysulphate may contain 0.10–3.0, e.g. 0.45–3.0, sulphate groups per monosaccharide unit.

When using dextran sulphate as the polysaccharide polysulphate the degree of substitution of sulphate groups is 0.10–3.0, preferably 0.90–3.0 per monosaccharide unit. When using dermatan sulphate or heparan sulphate the degree of substitution of sulphate groups is 0.45 to about 2.0 per monosaccharide unit.

The average molecular weight of the polysaccharide polysulphate is not critical. Thus water-soluble polysaccharide polysulphates having a molecular weight of from about 1,000 up to at least 10,000,000 may be used. It is also possible to use water-soluble and water-insoluble cross-linked polysaccharide polysulphates.

If desired the polysaccharide polysulphate may be coupled to a water-insoluble carrier, such as a cross-linked dextran. It is also possible to couple the polysaccharide polysulphate to the corresponding unsubstituted polysaccharide. In that case the degree of substitution of sulphate groups is calculated on the substituted portion of such a product.

When carrying out the method according to the invention it is convenient to dilute the sample with saline or with a buffer. A dilution of more than about 1/10, preferably more than 1/30 is then used. Thereby, interference by agents known to adversely affect the coagulation system is effectively eliminated.

The incubation time used is dependent on the concentrations of the reactants in the incubation solution and also on the incubation temperature. It is easy for the skilled art worker to determine the optimum time in each case. The incubation temperature may suitably be varied from about 20° C. to about 37° C.

In the method it is convenient to use a pH of about 7.0–8.0. The amounts of polysaccharide polysulphate and activated factor X (Xa) are not critical. Thus it is suitable to use from 1 to 2000 $\mu$g/ml of polysaccharide polysulphate and from 1 to 10 units of Xa/ml. It is easy for those skilled in the art to determine the optimun concentrations in each case.

During the investigations of the present invention it has been shown that polysaccharide polysulphates may exhibit three major properties in blood coagulation (a) ability to overcome the inhibitory action of a human plasma component under neutralization mechanism of Xa by Xa-inhibitor (b) a weak heparin-like activity (c) a synergistic effect on the anticoagulant activity of trace amounts of heparin When carrying out the determination of Xa-inhibitor according to the present invention it may be suitable to neutralize the heparin-like activity of the polysaccharide polysulphate by adding a heparin neutralizer, like hexadimethrine bromide (Polybrene® from Abbott Laboratories, U.S.A.) or protamine salts, to the substrate plasma. Otherwise the clotting times will be unduly long.

Making use of the synergistic effect of the polysaccharide polysulphates on the anticoagulant activity of trace amounts of heparin the method according to the present invention may be used for an ultra-sensitive heparin test. A small amount of a polysaccharide polysulphate added to the test plasma which amount by itself, has no measurable heparin-like anticoagulant activity, enhances the heparin anticoagulant activity by several folds.

The invention will now be described in greater detail with reference to the following concrete working examples, which however do not limit the scope of the invention as it is defined in the claims.

EXAMPLE 1

For the determination of the XaI biological activity in blood plasma the following reagents were prepared.

(a) Bovine plasma activated Factor X (factor Xa). This reagent can be prepared by any method described in the literature. Basically a Factor X rich fraction is prepared from bovine plasma known as $BaSO_4$ eluate which is then treated with either Russel's viper venom or trypsin in the presence of calcium chloride. Factor X is then activated to Factor Xa. Then the activated mixture is chromatographed on an anion exchange column (e.g. DEAE-cellulose) according to Yin et al. in J. Biol. Chem. 243 (1968) p. 112 to isolate the Factor Xa free of other substances, especially the venom. The isolated Factor Xa is then stabilized in crystallized bovine serum albumin according to Yin et al. in J. Lab. Clin. Med. 81 (1973) p. 298 (Ref. 1).

(b) Anticoagulant-free bovine plasma (AFBP) prepared according to Yin et al. (Ref. 1) and mixed with cephalin (mammalian brain or soybean phosphatides). This mixture is subsequently referred to as AFBP-cephalin.

(c) Buffer-Mono Tris (hydroxymethyl) aminomethane maleate. A concentration of 0.02 M, pH 7.5 was employed in the test.

0.5 ml of diluted citrated human plasma [diluted with saline (e.g. 0.9% NaCl) to 1:50] was added to a test tube containing 0.4 ml of the sodium salt of a solution of dextran sulphate ($\overline{M}_w$ = 20.000, degree of substitution = 1.15 sulphate groups per monosaccharide unit) in the buffer. The concentration of dextran sulphate was 50 µg/ml of this incubation mixture. This mixture was then pre-warmed in a 37° C. water bath for one minute after which 0.1 ml of factor Xa were added and a first stop watch was started.

Ninety seconds after the addition of Xa, 0.1 ml of the incubation mixture were transferred to a second clean test tube that had been pre-warmed in the 37° C. water bath. At 110 seconds on the first stop watch, 0.1 ml of 0.03 M $CaCl_2$ were added to that second test tube. At exactly 120 seconds on the first stop watch, 0.2 ml of the AFBP-cephalin mixture, were forcefully blown into said second test tube and a second stop watch was simultaneously started. The time (in seconds) required to form a solid clot was then recorded. A XaI activity calibration curve was then constructed by making a serial doubling dilution of the plasma sample, using the 1:50 initial dilution as 100% activity. (Table 1).

Analogously another XaI activity calibration curve was established by using a different initial plasma dilution and concentration of dextran sulphate (Table 1).

Table 1

| Plasma dilution taken as 100 % XaI activity | % XaI activity | clotting time in seconds |
|---|---|---|
| $\frac{1}{50}$ | 100 % | 79,5 |
| using 50 µg dextransulphate per milliliter of incubation mixture | 50 % | 53.0 |
| | 25 % | 38.5 |
| | 12.5 % | 31.0 |
| | 6.25 % | 27.0 |
| | 0 % | 24.5 |
| $\frac{1}{100}$ | 100 % | 58 |
| using 33 µg dextransulphate per milliliter of incubation mixture | 50 % | 39 |
| | 25 % | 32 |
| | 12,5 % | 27.5 |
| | 0 % | 24 |

This table clearly indicates that an enzyme-inhibitor (Xa — XaI) interaction is measured with high sensitivity.

EXAMPLE 2

The procedure according to Example 1 was repeated when using a solution of the sodium salt of a dermatan sulphate $M_w$ = 30.000–50.000 degree of substitution. 1.0 sulphate group per disaccharide unit) instead of the dextran sulphate. The following results were obtained:

Table 2

| Plasma dilution taken as 100 % XaI activity | % XaI activity | clotting time in seconds |
|---|---|---|
| $\frac{1}{100}$ | 100 % | 57,5 |
| using 15 µg dermatan sulphate per milliliter incubation mixture | 50 % | 40.0 |
| | 25 % | 27.5 |
| | 12.5 % | 23.0 |
| | 0 % | 17.4 |

This table clearly indicates that an enzyme-inhibitor (Xa - XaI) interaction is measured with high sensitivity.

EXAMPLE 3

To illustrate the possibility of the determination of low concentrations of heparin by the method according to the present invention the procedure of Example I was repeated with the following exceptions:

(a) Undiluted plasma was used in the incubation mixture.

(b) The plasma contained heparin in a known concentration of 0.006 units/ml.

The addition of the sodium salt of dextran sulphate ($\overline{M}_w$ = 20.000, degree of substitution 1.15 sulphate groups per monosaccharide unit) to a final concentration of 10 µg/ml in the incubation mixture, resulted in a detection of a heparin-like activity corresponding to 0.05 units/ml. This proves that the sensitivity of a heparin test according to these principles could be increased approximately by a factor of ten. 10 µg of dextran sulphate by itself does not have any measurable heparin-like anticoagulant activity in this test system.

We claim:

1. A method for the in vitro determination of the biological activity of Factor Xa inhibitor (XaI) in blood, which includes the steps of
   (1) incubating a diluted blood plasma sample with constant known concentrations of excess Xa and polysaccharide polysulfate for a predetermined period, said polysaccharide polysulfate exhibiting the following properties
(a) ability to overcome the inhibitory action of a human plasma component under neutralization mechanism of Xa by Xa inhibitor,
(b) a weak heparin-like activity, and
(c) a synergistic effect on the anticoagulant activity of trace amounts of heparin, and (2) after the predetermined incubation period measuring the residual Xa activity (i.e. Xa activity remaining in the incubation mixture that is not neutralized by the plasma XaI), the mechanism of reaction between the XaI and the Xa in the presence of said polysaccharide polysulfate being rate limiting (i.e. incubation time dependent).

2. A method as set forth in claim 1 wherein the residual amount of factor Xa activity is determined by measuring the clotting time.

3. A method as set forth in claim 1 wherein the residual amount of factor Xa activity is determined by measuring its esterase or the amidolytic activity.

4. A method as set forth in claim 1 wherein the polysaccharide polysulphate has 0.10-3.0 sulphate groups per monosaccharide unit.

5. A method as set forth in claim 4 wherein the polysaccharide polysulphate is a dextran sulphate having 0.10-3.0 sulphate groups per monosaccharide unit.

6. A method as set forth in claim 4 wherein the polysaccharide polysulphate is a dermatan sulphate or a heparan sulphate having 0.45-2.0 sulphate groups per monosaccharide unit.

7. A method as set forth in claim 1 wherein the polysaccharide polysulphate is coupled to a water-insoluble carrier.

* * * * *